United States Patent [19]

Mochida et al.

[11] 4,332,788

[45] Jun. 1, 1982

[54] METHOD OF DETERMINING AN ANTIGEN, ANTIBODY FOR ANTIGEN-ANTIBODY COMPLEX INCLUDING FIXING THE AGGREGATES THEREOF

[75] Inventors: Ei Mochida, Tokyo; Hiroyuki Shinkai, Kawagoe; Takashi Kudo, Tokyo; Toshiyuki Sugawara, Urawa, all of Japan

[73] Assignee: Mochida Seiyaku Kabushiki Kaisha, Tokyo, Japan

[21] Appl. No.: 152,390

[22] Filed: May 22, 1980

[30] Foreign Application Priority Data

Jun. 5, 1979 [JP] Japan .................................. 54/70371

[51] Int. Cl.³ ...................... G01J 3/42; G01N 21/75; G01N 31/06; G01N 33/52
[52] U.S. Cl. .................................. 424/12; 23/230 B; 356/39; 356/319; 356/434; 356/442; 424/8; 424/11; 424/13; 424/78
[58] Field of Search ..................... 424/3, 8, 11, 12, 13, 424/78; 23/230 B; 356/39, 300, 319, 432, 433, 434, 441, 442

[56] References Cited

U.S. PATENT DOCUMENTS 4,185,084  1/1980  Mochida ................................ 424/1

OTHER PUBLICATIONS

Bonnefoy, CR Acad Sci Paris, vol. 283, Jul. 5, 1976, Ser D, pp. 115-118 (translation enclosed).

*Primary Examiner*—Anna P. Fagelson
*Attorney, Agent, or Firm*—Stevens, Davis, Miller & Mosher

[57] ABSTRACT

A method for the quantification of an antigen, antibody, or antigen-antibody complex in a sample solution involving measuring the results of an immunochemical agglutination reaction or an agglutination inhibition reaction by spectrophotometry, wherein after the initiation of the agglutination between the antigen, antibody, or antigen-antibody complex to be determined and sensitized carrier particles to which a substance specifically bindable to the said antigen, antibody, or antigen-antibody complex is bound, a fixing compound is added to fix aggregates formed by the agglutination. A measuring reagent kit or pack includes all the components for use in carrying out the above method.

16 Claims, 10 Drawing Figures

METHOD OF DETERMINING AN ANTIGEN, ANTIBODY FOR ANTIGEN-ANTIBODY COMPLEX INCLUDING FIXING THE AGGREGATES THEREOF

BACKGROUND OF THE INVENTION

It is well known that the determination of the presence of an antigen or antibody in body fluids has great significance in the diagnosis of remedy of diseases or abnormal or pathological states or conditions. Recently, certain antigen-antibody complexes or conjugates associated closely with autoimmune diseases such as systemic lupus erthematosus, rheumatoid arthritis, and certain glomerular nephritis have been found. Accordingly, it has currently become more significant to determine an antigen, antibody, or antigen-antibody complex or conjugate in body fluids to aid in the diagnosis or remedy of physiological or pathological states or conditions in both human beings and animals.

It will be understood that the terms "antigen or antibody" and "antigens or antibodies" when employed herein include an "antigen-antibody complex" and "antigen-antibody complexes" unless otherwise specifically noted to the contrary. It also will be understood that the terms "antigen-antibody complex" and "antigen-antibody complexes" when employed herein include an "antigen-antibody conjugate" and "antigen-antibody conjugates" unless otherwise stated.

One of the conventional methods for determining antigens, antibodies, or antigen-antibody complexes is the socalled slide-type method. This method consists of two procedures. The first procedure is to bind a substance that is specifically bindable to an antigen or antibody onto the surface of a carrier that is composed of fine-grained insoluble particles and suspend the bound substance in a suitable liquid. The second procedure is to mix the suspension, which is prepared in the first step, with a sample solution that contains the antigen or antibody to be determined. With this method, various kinds of antigens or antibodies can be determined semi-quantitatively by observing the agglutination of the suspension.

There are also methods known for quantitatively determining an antigen or antibody to be determined in a sample solution by spectrophotometrically or electrically measuring the results of the agglutination reaction, using the same materials as used in the slide-type method (Croatica Chemica Acta, 42, 457–466 (1970); European Journal of Biochemistry, 20, 533–560 (1971); Japanese patent application (Lay-Open) No. 24,015/1978; Japanese patent application (Lay-Open) No. 69,824/1978).

Of these quantitative measuring methods, the method for spectrophotometrically measuring the results of the agglutination reaction is outlined as follows: A substance specifically bindable to an antigen or antibody to be determined, such as, for example, the antigen or antibody corresponding to the antigen or antibody to be determined, is physically or chemically bound to finely divided, insoluble carrier particles to provide sensitized carrier particles which are then suspended in an appropriate liquid and reacted with a sample solution containing the antigen or antibody to be determined under predetermined conditions, and the reaction mixture is measured with respect to its absorbancy or turbidity to quantitatively determine the antigen or antibody to be determined present in the sample solution. It will be understood that the terms "sensitized carrier particles" or "sensitized carrier particle" referred to herein mean the insoluble carrier particle sensitized by binding thereto such a substance as being specifically bindable to the antigen or antibody to be determined.

The afore-mentioned spectrophotometric method, however, encounters difficulties in providing an accurate quantitative determination of the antigen or antibody. In this method, the absorbancy or turbidity of a reaction mixture is measured while the reaction is still proceeding therein so that the absorbancy or turbidity thereof will tend to vary to a great extent with the lapse of time because the reaction proceeds even after the preselected period of reaction. Accordingly, this method requires the measurement of absorbancy or turbidity to be effected immediately after the predetermined period of reaction has lapsed; otherwise, variations in measured values will be so great that accuracy in measurement will be decreased. These difficulties will cause problems in the practical application of this method to the actual quantitative measurement of an antigen or antibody.

In conventional quantitative methods, the reaction of a sensitized carrier particle suspension and a sample solution often may be carried out with stirring in order to accelerate the reaction. However, aggregates formed by the antigen-antibody reaction may be decomposed easily by mechanical impacts or stimula when they exceed the binding power in the aggregates produced by the antigen-antibody reaction. Furthermore, the extent to which the aggregates are decomposed varies greatly with stirring conditions so that accuracy or sensitivity in measurement will be decreased.

In order to provide a spectrophotometric procedure having improved sensitivity and accuracy in determining an antigen or antibody to be determined in a sample solution, extensive studies have been made with the assumption that various problems and difficulties associated with conventional spectrophotometric techniques would be overcome if the agglutination reaction or the agglutination inhibition reaction were ceased at an appropriate stage of reaction and aggregates formed by the reaction were fixed, thereby preventing them from decomposing upon encountering mechanical means such as stirring.

As a result, it has been found that the employment of a fixing compound can cease the agglutination or agglutination inhibition reaction at a desired stage of reaction and prevent the aggregates formed thereby from being decomposed.

SUMMARY OF THE INVENTION

Accordingly, it is the primary object of the present invention to provide a spectrophotometric method for quantitatively determining an antigen or antibody with high sensitivity and accuracy.

It is another object of the present invention to provide a method for the spectrophotometric quantification of an antigen or antibody in a sample solution, in which the agglutination reaction or the agglutination inhibition reaction can be ceased at a desired state of reaction.

It is a further object of the present invention to provide a spectrophotometric method for the quantification of an antigen or antibody in a sample solution, in which aggregates formed by the agglutination reaction or the agglutination inhibition reaction are fixed to thereby prevent decomposition upon encountering mechanical means such as stirring.

It is a further object of the present invention to provide a reagent kit or pack for use in spectrophotometrically quantifying an antigen or antibody.

It is a further object of the present invention to provide a reagent kit or pack of the type applicable to the method according to present invention.

Further objects and features of the invention will be apparent from the following description of the accompanying drawings and its preferred embodiments.

BRIEF DESCRIPTION OF THE DRAWINGS

In order that the present invention may be better understood, one embodiment thereof will now be described purely by way of illustration and example, with reference to the accompanying drawings in which.

DETAILED DESCRIPTION OF THE INVENTION

The present invention relates to a method of determining an antigen, antibody, or antigen-antibody complex or conjugate and a reagent kit or pack for use in determining the same.

The immunochemical reactions on which the method according to the present invention are based may include the immunochemical agglutination reaction and the agglutination inhibition reaction. The method based on the immunochemical agglutination reaction according to the present invention comprises carrying out the immunochemical agglutination reaction of at least one member selected from antigens, antibodies, and antigen-antibody complexes to be determined with sensitized carrier particles obtained by binding to insoluble carrier particles an antigen or antibody corresponding to the antigen or antibody to be determined and measuring the reaction mixture with respect to its absorbancy or turbidity by irradiation of light having appropriate wavelengths. On the other hand, the method based on the agglutination inhibition reaction according to the present invention involves an immunochemical agglutination inhibition reaction in which an antigen or antibody to be determined inhibits the immunochemical agglutination reaction of the insoluble carrier particles with an agglutinating agent, and measurement of the reaction mixture in the same manner as above.

According to the present invention, the method based on the immunochemical agglutination reaction may be carried out in the manner as will be described more in detail. The method, on the other hand, based on the immunochemical agglutination inhibition reaction may be carried out in substantially the same manner as in the agglutination reaction unless otherwise specifically stated to the contrary.

The measuring method on which one embodiment of the method according to the present invention is based involves the steps of (1) causing an antigen-antibody reaction between (a) sensitized carrier particles as the first component and (b) an antigen, antibody, or antigen-antibody complex or conjugate as the second component in a sample solution, said first component being formed by binding (I) one substance selected from the group consisting of antigens, antibodies, and antigen-antibody complexes corresponding to the antigens, antibodies, and antigen-antibody complexes and conjugates to be determined to (II) finely divided insoluble carrier particles so that at least two units of said substances are bound to each particulate carrier and said second component being capable of causing the immunochemical agglutination reaction with the substance bound to the sensitized carrier particles, fixing aggregates formed by the antigen-antibody reaction by addition of a fixing compound to the sample solution, and (2) irradiating the reaction mixture with a ray having an appropriate wavelength and measuring the absorbancy or turbidity of the reaction mixture, thereby to determine the quantity or concentration of the antigen or antibody to be determined.

In the immunochemical agglutination reaction which is the basis of the measuring method according to the present invention, an antigen or antibody specifically bindable to and, for example, corresponding to the antigen or antibody to be determined is first physically or chemically bound to finely divided insoluble carrier particles. A number of procedures for binding to finely divided carrier particles an antigen or antibody specifically bindable to the antigen or antibody to be determined are known. Generally, physically sorption procedures or chemically binding procedures are carried out (Japanese patent application Lay-Open No. 16,623/1972 and Japanese patent application Lay-Open No. 8,868/1973).

The carrier to be employed as the fine particle carrier according to the present invention may be any carrier which has been conventionally used as sensitized carrier particles for use in reagents for slide-type tests and include an organic polymer latex such as, for example, polystyrene latex, carboxylated polystyrene latex, styrene-divinyl benzene copolymer latex, hydroxylated or carboxylated styrene-divinyl benzene copolymer latex, polyvinyl alcohol latex, polyacrylic ester latex or vinyl acetate-acrylate copolymer, an inorganic material such as, for example, silica carbon black or alumina, or cells such as, for example, bacteria or erythrocytes.

A suspension of the sentitized carrier particles may be prepared by suspending the sensitized carrier particles in an appropriate solution conventionally used for the purpose of providing an suspension of sensitized carrier particles. The sensitized carrier particles may be suspended therein in amounts ranging from about 0.1 to about 200 miligrams, preferably from about 1 to about 50 milligrams per milliliter of the solution. The solution in which the sensitized carrier particles is suspended may include water or any other liquid which doe not adversely affect the reaction and conditions involved with the measuring method according to the present invention.

A solution containing an antigen or antibody to be determined is then added to the sensitized carrier particle suspension to cause the immunochemical agglutination reaction of the antigen or antibody to be determined with the sensitized carrier particles. An amount as small as approximately 0.05 to 1.0 milliliter of the reaction mixtured obtained by the immunochemical agglutination reaction may be generally employed for this purpose. When the amount of the reaction mixture is too small so that the measurement of the reaction mixture with respect to its absorbancy or turbidity would be difficult, an appropriate solvent such as a physiological saline solution may be added thereto, after completion of the fixation of the immunochemical agglutination reaction by a fixing compound, to increase the volume of the reaction mixture so that the measurement may be effected with respect to the absorbancy of the reaction mixture.

Temperatures at which the sensitized carrier particle suspension is allowed to react with a sample solution are not particularly limited and may generally be any arbitrary temperature at which the antigen-antibody reaction is effected. Times for which the above reaction of the sensitized carrier particle suspension with the sample solution may be generally from approximately one minute to 24 hours, but preferably from approximately three minutes to 120 minutes where sensitivity and accuracy of measurement and practical convenience are taken into consideration. In order to make the reaction proceed homogeneously and smoothly, it is preferred that the reaction mixture is stirred gradually and slowly.

According to the present invention, a fixing compound is used to stop the antigen-antibody reaction causing the agglutination of the sensitized carrier particles in the suspension with the antigen or antibody to be determined.

The fixing compounds to be used according to the present invention may include polyfunctional compounds such as, for example, carbodiimides, e.g., 1-ethyl-3-(3-dimethyl-aminopropyl)-carbondiimide (hereinafter referred to as "propyl carbodiimide") and 1-cyclohexyl-3-(2-morpholinoethyl)-carbodiimide (hereinafter referred to as "morpholino carbodiimide"), dialdehydes, e.g., glutaraldehyde and succinaldehyde, acylating agents, e.g., N-ethyl-5-phenylisoxazonium-3′sulfonate, succinyl chloride, and the like, and also include protein-denaturing agents such as tannic acid, formalin, perchloric acid, trichloroacetic acid, thiocyanic acid and thioglycolic acid, and the like.

The fixing compounds to be used according to the present invention may be added to the reaction system at any time from the start to the completion of the agglutination reaction. In general, the fixing compound that is presented in this invention will be added after reacting the suspension reagent with a sample solution for a certain time-period, which will be determined in consideration to the system being employed. However, the fixing compound may be added to the system together with the other constituents in order to simplify and shorten the reaction steps.

The period of time required for the fixation of the aggregates and the optimum concentration of the fixing compound necessary for the fixation thereof have a correlation with each other and, further may be varied depending upon the kind of the fixing compound so that they may not be generally limited to particular ones. Partically, the period of time for fixation may range from about 3 to about 120 minutes, and the optimum concentration of the fixing compounds at the time of fixation may be preferably from approximately 0.1 to 40 percent for propyl carbodiimide, from approximately 0.1 to 5 percent for morpholino carbodiimide, from approximately 0.1 to 20 percent for glutaraldehyde, and from approximately 1 to 30 percent for formalin. The concentration of the fixing compound, however, may be somewhat lower where the fixing compound is added to the system together with the sensitized carrier particle suspension and the sample solution.

The amount of addition of the fixing compound to the reaction system according to the present invention may generally range from approximately 0.001 to 10 milliliter and preferably from approximately 0.01 to 3 milliliter with respect to the reaction mixture to be measured.

The proceedings of the reaction may substantially be ceased by dilution of the reaction mixture because it tends to lower the velocity of reaction. When the large amount of solution dissolving fixing compounds is added to the reaction system, it may effect the stop of the reaction proceeding and the fixation of the aggregates simultaneously. Accordingly, when the reaction mixture is diluted, the fixing compound may be added in a concentration sufficient to merely fix the aggregate so that it does not necessarily stop the antigen-antibody reaction.

The buffer solution which may be employed for diluting the reaction mixture at an appropriate concentration is one customarily used in the field of immunochemistry and includes, for example, a glycine-buffered saline solution, a phosphate-buffered saline solution and a borate-buffered saline solution. An appropriate amount of a protein such as bovine serum albumin and/or rabbit serum globulin may be added to such a buffer solution in order to enhance the reproducibility of the reaction. The addition of the buffer solution also may serve as maintaining the reaction system at an appropriate pH and ionic strength.

After the fixation of the aggregates is completed, the reaction mixture containing the aggregates is subjected to measurement of its absorbancy by conventional methods. Although any rays having wavelengths in the range of from 320 to 2400 nm, and preferably from 400 to 900 nm may be employed, an appropriate wavelength for measurement may be conveniently chosen from within the above wavelength range because the appropriate wavelength may be varied depending upon the kinds of constituents contained in a sample solution and the kinds of fine particle carrier and/or its particle sizes. The turbidity of the reaction mixture may also be measured in place of the absorbancy in a conventional manner.

The quantification of the antigen or antibody to be determined in the reaction mixture may be effected by comparison with a standard curve of the antigen or antibody to be determined. In order to plot the standard curve of each of the antigen or antibody to be determined, a series of procedures may be carried out by dissolving a reference substance identical per se to or identical in reactivity to the antigen or antibody to be determined in varying amounts of an appropriate buffer solution as mentioned above to provide a standard test solution with a given amount of the sensitized carrier particle suspension under predetermined conditions, immediately thereafter adding the fixing compound in order to stop the reaction from proceeding so that the aggregates formed are fixed, and measuring the absorbancy or turbidity of the reaction mixture in a measuring cell, which may be diluted with an appropriate liquid or buffer solution if necessary. The standard curve may be drawn with respect to the relationship of the amount or concentration of the standard substance with its absorbancy or turbidity. The quantification of the antigen or antibody to be determined may be carried out by reacting the sensitized carrier particle with an unknown sample in substantially the same manner and under substantially the same conditions as in the case of the case of the standard curve for the standard sample solution and by measuring the absorbancy or turbidity of the reaction mixture, and comparing the test results with the standard curve so prepared, thereby enabling the quantification of the antigen or antibody to be determined in the unknown sample.

In order to increase the measurement sensitivity, the use of a sensitized carrier particle suspension having a somewhat higher concentration is preferred.

According to the present invention, a relatively high concentration of the sensitized carrier particle suspension may be used so that the meansurement sensitivity can be improved.

In conventional measuring methods, the reaction mixture is subjected directly to measurement without being diluted because the dilution of the reaction mixture may destroy the aggregates formed. Accordingly, when the concentration of the suspension is too high, it is difficult to measure the reaction mixture so that the utilization of the conventional measuring methods is limited to a reaction mixture where the concentration of the suspension is lower than 0.6 percent by weight (Japanese patent application Lay-Open No. 24,015/1978). However, in the present invention, the reaction mixture may be employed even where it is diluted, if necessary, so that the present invention may provide the highest reaction sensitivity even when the concentration of the suspension is about 1 percent by weight.

The method based on the immunochemical agglutination inhibition reaction according to the present invention involves measuring changes in the absorbancy or turbidity caused by the immunochemical agglutination inhibition reaction in which the antigen or antibody to be determined inhibits the immunochemical agglutination reaction of the above insoluble carrier particles with an agglutinating agent.

The agglutinating agent to be used in one embodiment of the present invention is an agent which can cause induction for the agglutination of the sensitized carrier particle suspension where no or little or a very small amount of an antigen or antibody to be determined is present in a sample solution. It may generally include an antigen or antibody specifically bindable to the sensitized carrier particles and an antigen or antibody which is bound to the insoluble fine particle carrier.

The measuring method on which the other embodiment of the method according to the present invention involves causing the antigen-antibody reaction among sensitized carrier particles as the first component, an antigen or antibody to be determined as the second component, and an agglutinating agent as the third component, said first component being formed by binding one substance selected from the group consisting of antigens, antibodies, and antigen-antibody complexes corresponding to the antigens, antibodies, and antigen-antibody complexes and conjugates to be determined to finely divided insoluble carrier particles so that at least two units of said substances are bound to each particulate carrier, said second component being capable of causing the immunochemical agglutination reaction with the substance bound to the sensitized carrier particles, and said third component being at least one substance selected from the group consisting of antigens, antibodies, and antigen-antibody complexes capable of causing the immunochemical reaction with said first component, fixing aggregates formed by the antigen-antibody reaction by addition of a fixing compound to the sample solution, and irradiating the reaction mixture with a ray having an appropriate wavelength and measuring the absorbancy or turbidity of the reaction mixture, thereby to determine the quantity or concentration of the antigen or antibody to be determined.

To the sample solution to which the agglutinating agent was added is then added a given amount of the fixing compound. The addition of the fixing compound may be effected immediately after the inhibition of the antigen-antibody reaction. It may be possible, however, to add the agglutinating agent together with the other ingredients necessary for the measuring method according to the present invention based on the immunochemical agglutination inhibition reaction in order to simplify and shorten the procedure.

When the intended antigen-antibody reaction is an agglutination reaction, the measurement reagent kit or pack according to the present invention comprises (a) a suspension of sensitized carrier particles, (b) a buffer solution and (c) a fixing compound. When the intended antigen-antibody reaction is an agglutination inhibition reaction, the measurement reagent kit or pack according to the present invention comprises (a) a suspension of sensitized carrier particles, (b) a buffer solution, (c) an agglutinating agent, and (d) a fixing compound.

Some or all of the reagents of the measurement kit of the present invention may be freeze-dried reagents. In this case, an appropriate solvent may be attached to the measurement kit so that it is used for dissolving the freeze-dried reagents when the kit is actually used. In order to conveniently use the measurement kit of the present invention, a test tube, a pipette, and other accessory means may be attached to the measurement kit.

As the antigen or antibody that can be determined according to the method and measurement kit of the present invention, there can be mentioned protein hormones such as human chorionic gonadotrophin, insulin, and human growth hormone, protein substances such as α-fetoprotein, hepatitis B virus (HBs) immunoglobulin, antigen-antibody complexes, ceruloplasmin and transferrin, and haptenes such as thyroxine, testosterone, phenitoine, and phenobarbital.

The method according to the present invention has the following advantages.

Since the antigen-antibody reaction is stopped from proceeding by adding the fixing compound to the reaction mixture, the reaction is not further advanced while the absorbancy is being measured. Accordingly, variations of the measured values can be reduced and the measurement accuracy can be improved.

Since the aggregates formed by the reaction are fixed by the fixing compound, the mechanical strength of the aggregates is increased and disintegration of the once-formed aggregates by agitation of the reaction mixture or transfer of the reaction mixture to, for example, a cell for the measurement of the absorbancy or turbidity, can be remarkably reduced. Accordingly, variation of the measured values or reduction of the measurement accuracy attributed to disintegration of the once-formed aggregates can be prevented and the measurement can be accomplished with a high accuracy and a high sensitivity.

Another advantage of the present invention is that a special measurement apparatus is not required. More specifically, in the measurement method according to the present invention, since a further advance of the reaction is stopped by addition of the fixing compound, there is sufficient time to transfer the reaction mixture to a cell for the measurement of its absorbancy. Furthermore, since the formed aggregates are stably fixed, disintegration of the aggregates by transfer of the reaction can be effectively prevented. Accordingly, the operation may be carried out by using an ordinary reaction vessel and no special apparatus is required.

Still another advantage of the measurement method of the present invention is that all the steps for the measurement can be automated. More specifically, as described hereinbefore, the mechanical strength of the aggregates can be increased by addition of the fixing compound in the measurement method of the present invention and therefore, disintegration of the once-formed aggregates by transfer or agitation of the reaction mixture can be remarkably reduced. Accordingly, all the steps including the transferring and agitating steps can be automated.

A further advantage of the present invention is that quantitative measurement can be performed by using reagents for the conventional semi-quantitative measurement conducted on a slide. The measurement reagent kit or pack of the present invention is different from the conventional semi-quantitative measurement reagent kit only in the point that the fixing compound is added. Accordingly, when the measurement kit of the present invention is used, the reaction which has heretobefore been carried out on a slide is performed in a test tube and the absorbancy or turbidity is then measured according to the above-mentioned procedures, whereby the quantitative measurement can be accomplished.

Accordingly, if the fixing compound of the present invention is combined with the conventional reagent kit, the semi-quantitative slide test measurement method or the quantitative measurement method measuring the absorbancy can optionally be selected according to need.

Figure 1:
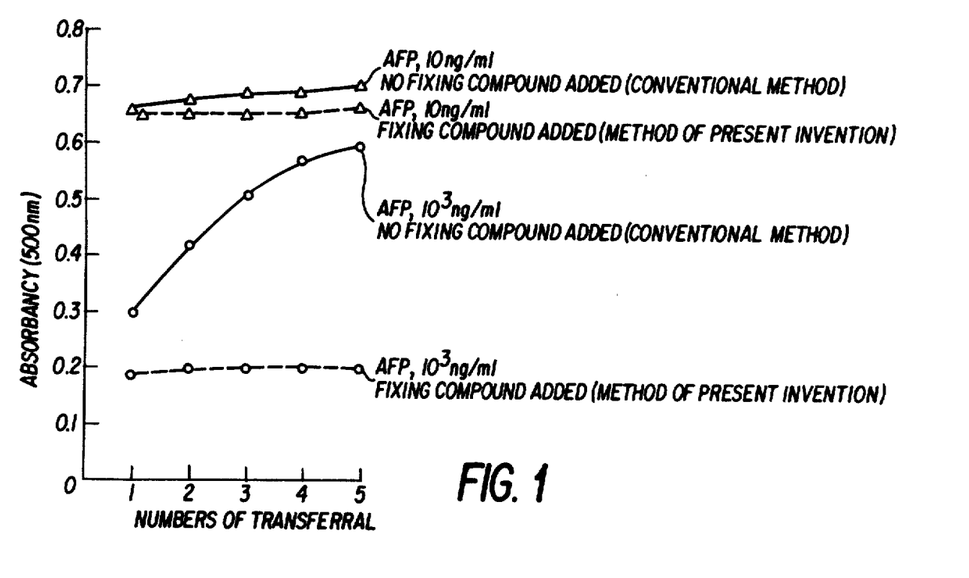
FIG. 1 is a diagram comparing the measurement method of the present invention with the conventional method with respect to the measurement accuracy.

FIG. 1 is a diagram comparing the measurement accuracy attainable by the method of the present invention in which the aggregates are fixed by adding a fixing compound to the reaction mixture, with the measurement accuracy attainable by the conventional method not using a fixing compound. More specifically, according to the method described in Example 1 given hereinafter, an anti-α-fetoprotein-sensitized latex reagent is reacted with a solution of a standard sample of α-fetoprotein, and a 10% propyl carbodiimide suspension is added as the fixing compound to the reaction mixture or is not added at all. In each case, transfer of the reaction mixture to a different vessel is repeated several times, and the absorbancy of the reaction mixture is measured to examine changes in the measured values by the above-mentioned repeated transfer. As will be apparent from FIG. 1, in the conventional method not using a fixing compound, the absorbancy is increased every time the reaction mixture is transferred. Accordingly, it is seen that the once-formed aggregates are disintegrated by a mechanical stimulus caused by the transfer.

In contrast, according to the method of the present invention using a fixing compound, the change of the measured value by the transfer is very small and it is seen that disintegration of the aggregates is hardly caused.

Figure 2:
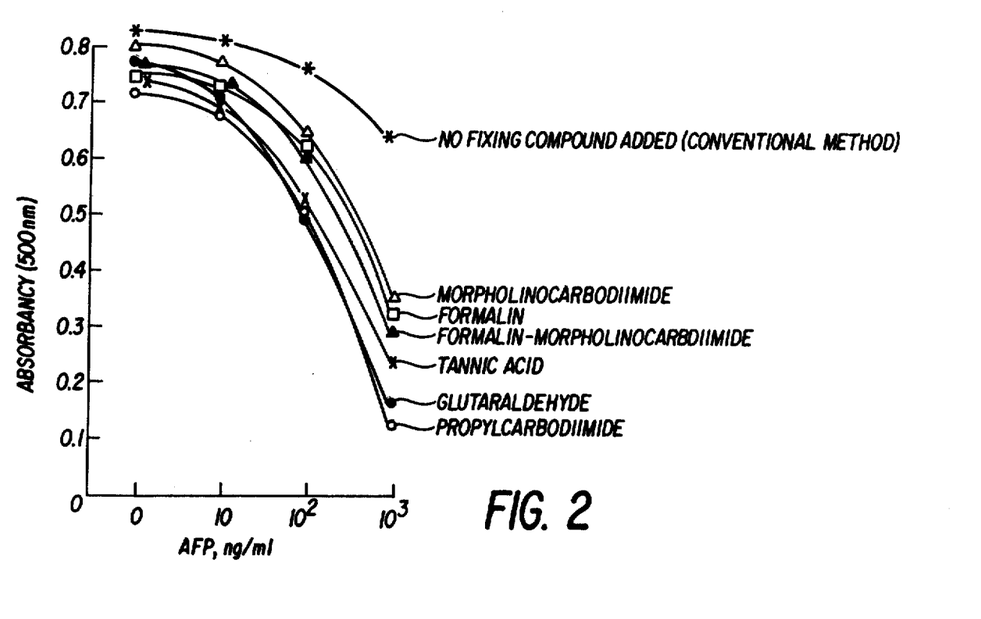
FIG. 2 is a diagram comparing the effects of various fixing compounds.

FIG. 2 shows the results of a comparison of the effects of various fixing compounds. More specifically, in the same manner as described above, an anti-α-fetoprotein antibodysensitized latex reagent is reacted with a standard sample solution of α-fetoprotein, and various fixing compounds are separately added to the reaction mixture to form standard curves, which are shown in FIG. 2. From FIG. 2, it is seen that when these fixing compounds are used, steeper standard curves are obtained and that high utility is attained by fixing aggregates formed by the antigen-antibody reaction.

Figure 3:
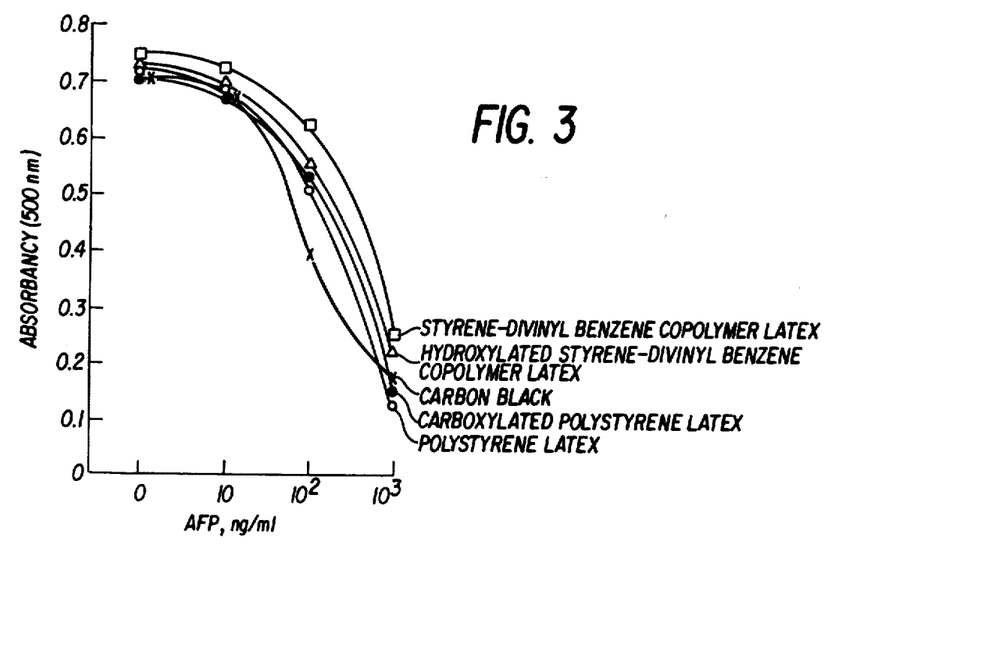
FIG. 3 is a diagram showing standard curves in the measurement method of the present invention using various fine particle carriers.

Examples of standard curves obtained by preparing reagents sensitized to an anti-α-fetoprotein antibody according to the method described in Example 1 given hereinafter by using various fine particle carriers and measuring a standard sample of α-fetoprotein by using these reagents are shown in FIG. 3.

From FIG. 3, it will readily be understood that similar standard curves can be obtained irrespective of the kind of carrier used.

The present invention will not be described in detail with reference to the following Examples, but it should be understood that they by no means limit the scope of the present invention.

EXAMPLE 1

This Example illustrates the measurement of α-fetoprotein (AFP).

(a) An anti-AFP antibody was dissolved at a concentration of 0.08% in a glycine-buffered saline solution (GBS) having a pH of 8.2, and 5 ml of the solution was added to 5 ml of a 10% suspension of polystyrene latex (a product of Dow Chemical Co., Midland, Michigan; mean particle size=0.48 μm) and incubation was carried out at 45° C. for 60 minutes to sensitize the polystyrene latex with the anti-AFP antibody. After the sensitization, the supernatant was removed by centrifugal separation and the precipitate was suspended in 50 ml of GBS containing 0.1% of bovine serum albumin (BSA) to form an anti-AFP antibody-sensitized latex reagent.

(b) AFT was extracted from ascitic fluid of a hepatoma patient according to the procedure of Nishi et al. [Cancer Res., 30, 2507-2523 (1970)], and the purified AFP was dissolved in a 0.1% solution of BSA at a concentration of $10^3$, $10^2$, $10^1$, or 0 ng/ml as a standard sample solution.

Figure 4:
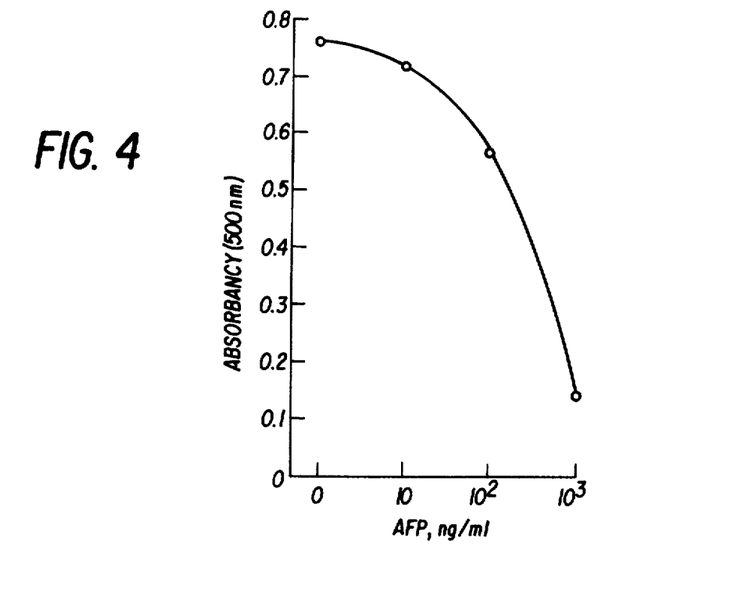
FIG. 4 is a diagram showing a standard curve for measuring α-fetoprotein in Example 1 of the present application.

Then 25 μl of the standard sample solution, 50 μl of GBS, and 25 μl of the anti-AFP antibody-sensitized latex reagent prepared in (a) above were put in a test tube. The reaction was carried out at room temperature for 40 minutes under mild shaking. After the reaction, 0.1 ml of a 10% propyl carbodiimide GBS solution as the fixing compound was then added to the reaction mixture and the reaction was carried out for 20 minutes under shaking. After the reaction, 4 ml of a physiological saline solution was added to the reaction mixture and the absorbancy at a wave length of 500 nm was measured by using a spectrophotometer (Hitachi Model 624 manufactured by Hitachi, Limited Tokyo, Japan). The measurement was made twice with respect to each standard solution. The obtained results were plotted on a graph to obtain a standard curve in FIG. 4.

(c) The concentration of AFP in the sera of hepatoma patients were determined in advance according to the semiquantitative method, and each serum was diluted appropriately based on the obtained results. 25 μl of the diluted serum was put into a test tube and the absorbancy was measured according to the procedures described in (b) above. The concentrations of AFP in the sera of the patients were determined from the obtained values respectively by using the standard curve formed in (b) above. The obtained results are shown in Table 1.

TABLE 1

| Patient No. | Sample | | | AFP Concentration (ng/ml) |
|---|---|---|---|---|
| | Material | Dilution Ratio (Times) | Absorbancy | |
| 1 | serum | 1 | 0.611 | 62 |
| 2 | serum | 40 | 0.541 | 4520 |
| 3 | serum | 40 | 0.581 | 3450 |
| 4 | serum | 1 | 0.321 | 298 |
| 5 | serum | 30 | 0.553 | 3600 |

EXAMPLE 2

This Example illustrates the measurement of human chorionic gonadotrophin (HCG).

(a) According to the procedures described in Example 1-(a), an anti-HCG antibody and a carboxylated polystyrene latex (a product of Dow Chemical Co.; mean particle size=0.25 μm) were mixed and incubated to form an anti-HCG antibody-sensitized latex reagent.

Figure 5:
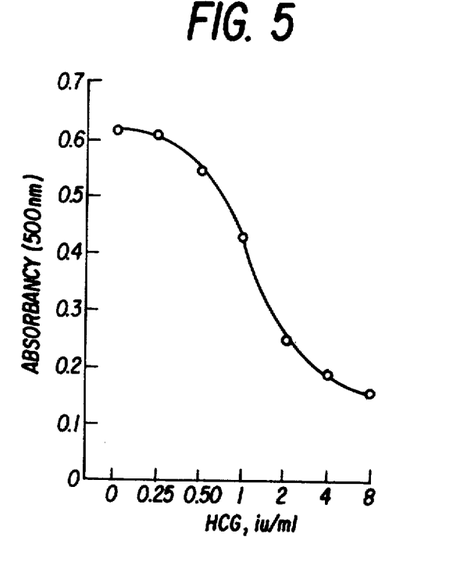
FIG. 5 is a diagram showing a standard curve for measuring human chorionic gonadotrophin in Example 2 of the present application.

(b) HCG (having a specific activity of 6000 iu/mg) was dissolved in GBS at concentrations of 8, 4, 2, 1, 0.5, and 0.25 iu/ml) as standard sample solutions. 25 μl of the standard sample solution, 50 μl of a buffer solution and 25 μl of the anti-HCG antibody-sensitized latex reagent prepared in (a) above were put into a test tube. The reaction was carried out at room temperature for 60 minutes under mild shaking. After the reaction, 4 ml of a 10% glutaraldehyde solution was added to the reaction mixture and the reaction was further carried out for 30 minutes. The absorbancy at 500 nm was measured to obtain a standard curve shown in FIG. 5.

(c) Human serum or urine was treated according to the procedures described in (b) above and the absorbancy was determined. Then, the amount of HCG in the serum or urine sample was determined based on the standard curve formed in (b) above. The obtained results are shown in Table 2. The results obtained by the slide-test method (minimum sensitivity: 1 iu/ml) and the radio-immunoassay method (RIA method) are also shown in Table 2 for reference.

TABLE 2

| Patient No. | Sample | | | HCG Concentration (iu/ml) | Slide Test Method | RIA Method (iu/ml) |
|---|---|---|---|---|---|---|
| | Material | Dilution Ratio (times) | Absorbancy (mean) | | | |
| 1 | urine | 1 | 0.589 | 0.28 | — | 0.41 |
| 2 | urine | 1 | 0.421 | 0.99 | + | 1.02 |
| 3 | urine | 1 | 0.458 | 0.86 | ± | 0.89 |
| 4 | urine | 1 | 0.212 | 2.93 | + | 3.21 |
| 5 | urine | 10 | 0.339 | 13.67 | ++ | 17.36 |
| 6 | serum | 1 | 0.543 | 0.54 | — | 0.66 |
| 7 | serum | 1 | 0.203 | 3.32 | ++ | 3.12 |
| 8 | serum | 1 | 0.551 | 0.86 | ± | 0.91 |
| 9 | serum | 1 | 0.458 | 0.50 | — | 0.57 |
| 10 | serum | 1 | 0.309 | 1.55 | + | 2.26 |

—: No. HCG or 1<iu/ml HCG
±: app. 1 iu/ml HCG
+: >1 ul/ml HCG
++: much greater than 1 iu/ml HCG

EXAMPLE 3

This Example illustrates an embodiment of the method based on the agglutination inhibition reaction.

(a) According to the procedures described in Example 1-(a), an hydroxylated styrene-divinylbenzene copolymer latex (a product of Rhone-Poulenc, Paris, France; mean particle size=0.33 μm) was sensitized with an anti-estriol antibody prepared by using an estriol-16,17dihemisuccinate/bovine serum albumin conjugated (hereinafter referred to as "$E_3$-BSA") to form an anti-estriol antibody-sensitized latex reagent.

Figure 6:
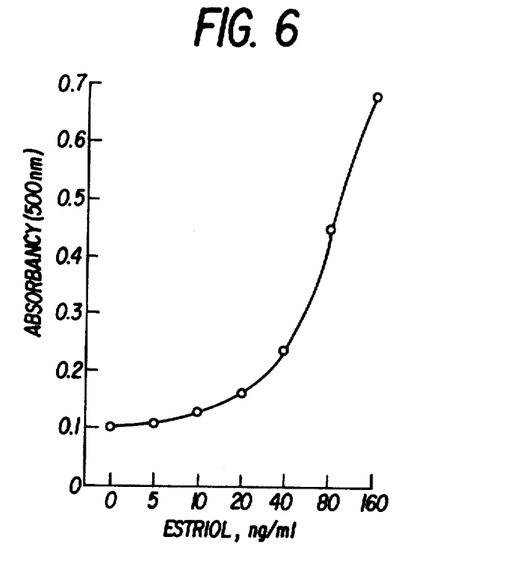
FIG. 6 is a diagram showing a standard curve for measuring estriol by the agglutination inhibition reaction in Example 3 of the present application.

(b) $E_3$-BSA was dissolved in a physiological saline solution at a concentration of 160, 80, 40, 20, 10, or 5 ng/ml as a standard solution. 25 μl of the anti-estriol antibody-sensitized latex reagent prepared in (a) above, 25 μl of a solution (concentration=100 μg/ml) of an estrone-17-(0-carboxymethyl)oxime/bovine serum albumin complex (hereinafter referred to as "$E_1$-BSA") as an agglutinating agent and 25 μl of the standard solution was added and reaction was carried out at room temperature for 40 minutes. After the reaction, 4 ml of a 10% propyl carbodiimide solution was added and the reaction was carried out for 20 minutes. Then, the absorbancy of the reaction mixture was measured and a standard curve shown in FIG. 6 was obtained.

(c) The urine of the pregnant woman was appropriately diluted with a physiological saline solution whose dilution ratio was decided by the results of pre-examining by the semiquantitative determination. According to the procedures described in (b) above, the concentration of estriol in the urine was determined quantitatively. The obtained results are shown in Table 3.

TABLE 3

| No. of Pregnant Woman | Weeks of Pregnancy | Sample | | Absorbancy | Estriol Concentration (mg/l) |
|---|---|---|---|---|---|
| | | Material | Dilution Ratio (Times) | | |
| 1 | 4 | urine | 1 | 0.455 | 0.08 |
| 2 | 16 | urine | 10 | 0.299 | 0.48 |
| 3 | 28 | urine | 50 | 0.200 | 1.21 |
| 4 | 31 | urine | 500 | 0.534 | 5.30 |
| 5 | 36 | urine | 1000 | 0.483 | 9.80 |

EXAMPLE 4

(a) A polystyrene latex was sensitized with denatured immunoglobulin (IgG) according to the procedure described in Example 1-(a), as a denatured IgG-sensitized latex reagent.

Figure 7:
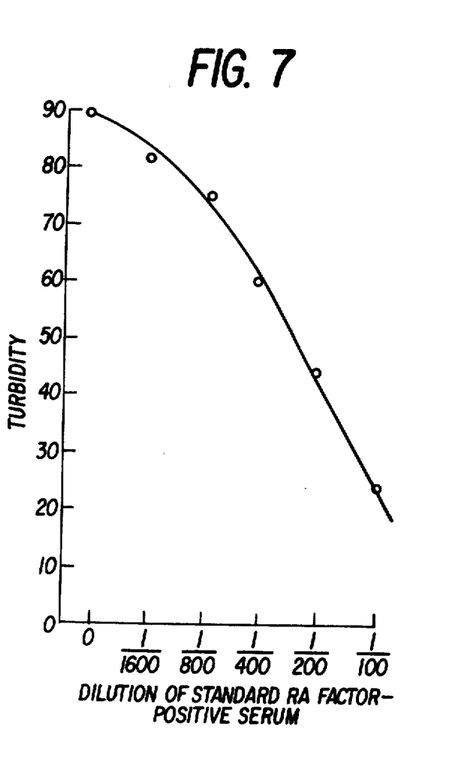
FIG. 7 is a diagram illustrating a standard curve for measuring the rheumatoid factor according to the turbidity method in Example 4 of the present application.

(b) Rheumatoid factor-positive serum as a standard sample was diluted at a dilution ratio of 1600, 800, 400, 200, and 100 times to prepare a standard sample solution. 25 μl of the standard sample solution, 50 μl of buffer solution, and 25 μl of the denatured IgG-sensitized latex reagent prepared in (a) above were put in a test tube, and the reaction was carried out at room temperature for 40 minutes. After the reaction, 0.1 ml of a 10% propyl carbodiimide solution was added and reaction was carried out for 20 minutes. Then, 4 ml of a physiological saline solution was added to the reaction mixture and the the turbidity was measured by a turbidimeter (Corona UT-11) while regarding the full scale as 100. An example of the standard curves is shown in FIG. 7.

(c) By using a patient serum instead of the standard solution, the rheumatoid factor in the serum was determined by the same way as described in (b) above. The obtained results are shown in Table 4.

TABLE 4

| Sample No. | Sample | Turbidity | Dilution Ratio (times) of Standard RA Factor-Positive Serum | Judgement |
|---|---|---|---|---|
| 1 | serum | 89.0 | 0 | − |
| 2 | serum | 66.8 | 700 | ++ |
| 3 | serum | 89.7 | 0 | − |
| 4 | serum | 56.5 | 300 | +++ |
| 5 | serum | 77.9 | 1000 | + |

−: negative in rheumatoid factor
+, ++, +++: positive in rheumatoid factor

EXAMPLE 5

(a) According to the procedures described in Example 1-(a), a polystyrene latex was sensitized with an antibody to human gamma-globulin (HGG) as an anti-HGG antibody-sensitized latex reagent.

Figure 8:
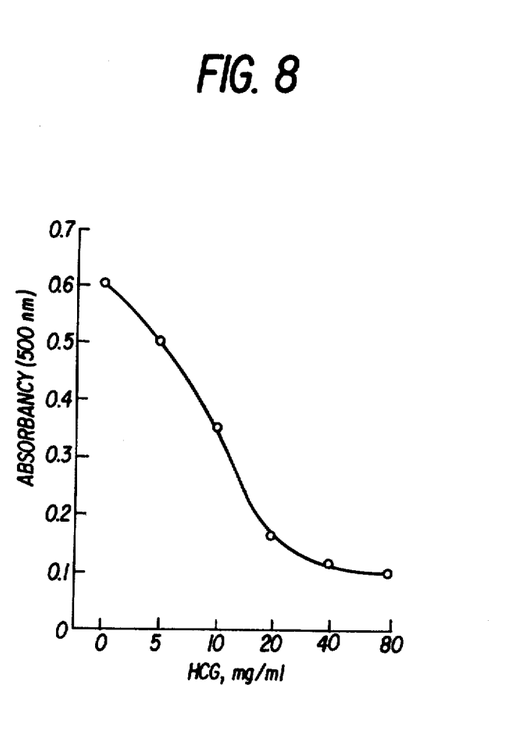
FIG. 8 is a diagram showing a standard curve for measuring human gamma-globulin in Example 5 of the present application.

(b) The standard sample solution was prepared by dissolving the HGG in a buffer solution at a concentration of 80, 40, 20, 10, and 5 mg/ml. 25 μl of the standard sample solution, 50 μl of a buffer solution, and 0.1 ml of a 1% propyl carbodiimide solution were put in a test tube, and 25 μl of the anti-HGG antibody-sensitized latex reagent prepared in (a) above was added and the reaction was carried out at room temperature for 40 minutes. After the reaction, 4 ml of a physiological saline solution was added and the absorbancy at 500 nm was measured. An example of the standard curves thus obtained is shown in FIG. 8. The concentration of HGG could be determined by utilizing the standard curve shown in FIG. 8.

EXAMPLE 6

Carbon black ("Show Black" manufactured by A. A. Chemical; mean particle size=0.02–0.04 μm) was suspended in GBS at a concentration of 10%. Then, 0.5 ml of the suspension was mixed with 2 ml of a solution of an anti-AFP antibody, and incubated at 56° C. for 20 minutes. After the incubation, the supernatant was removed by centrifugation, and the residual precipitate was suspended in 5.5 ml of GBS containing 0.1% BSA as an anti-AFP antibody-sensitized carbon black reagent.

Figure 9:
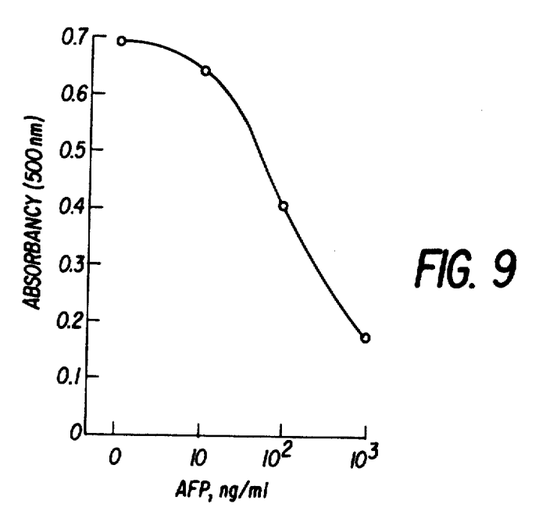
FIG. 9 is a diagram showing a standard curve for measuring α-fetoprotein in Example 6 of the present application.

(b) 25 μl of the AFP standard solution prepared in Example 1-(b), 50 μl of a buffer solution, and 25 μl of the anti-AFP antibody-sensitized carbon black reagent prepared in (a) above were put in a test tube, and reaction was carried out at room temperature for 10 minutes. After the reaction, 0.1 ml of a 10% propyl carbodiimide solution was added and reaction was carried out for 20 minutes. Then, 4 ml of a physiological saline solution was added to the reaction mixture and the absorbancy at 500 nm was measured. An example of standard curves is shown in FIG. 9. The concentration of AFP in serum could be determined by using the standard curve.

EXAMPLE 7

(a) According to the procedures described in Example 1-(a) an hydroxylated styrene-divinylbenzene copolymer latex was sensitized with $E_1$-BSA to prepare an $E_1$-BSA-sensitized latex reagent.

Figure 10:
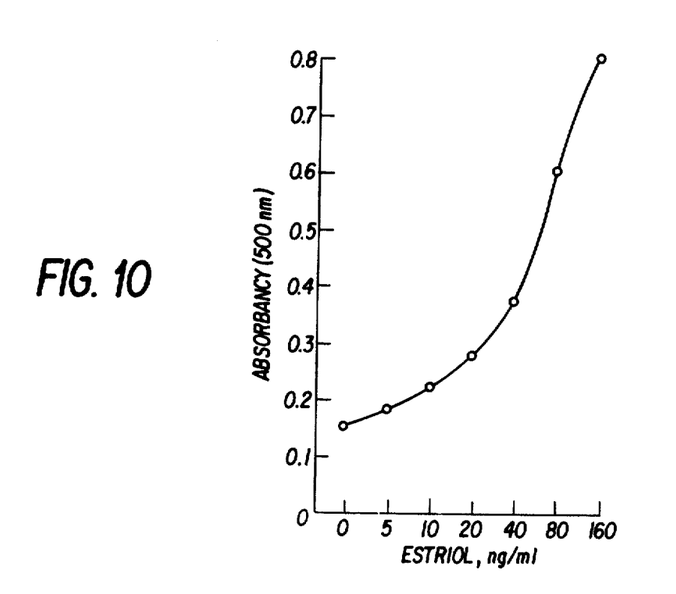
FIG. 10 is a diagram showing a standard curve for measuring estriol in Example 7 of the present application.

(b) 25 l of the $E_1$-BSA-sensitized latex reagent prepared in (a) above, 25 μl of a buffer solution, and 25 μl of the standard sample solution prepared in Example 3-(b) were put in a test tube, and 25 μl of the anti-estriol antibody-sensitized latex reagent prepared in Example 3-(a) was added and the subsequent procedures were made in the same manner as described in Example 3. A standard curve obtained is shown in FIG. 10.

EXAMPLE 8

According to the procedures described in Example 3, 25 μl of the anti-estriol antibody-sensitized latex reagent, 25 μl of the standard sample solution, 25 μl of the agglutinating agent, and 1 ml of a buffer solution were put in a test tube, and the reaction was carried out at room temperature for 40 minutes. After the reaction, 0.1 ml of a 10% propyl carbodiimide solution was added and reaction was carried out for 20 minutes. The absorbancy of the reaction mixture was measured to plot a standard curve. The above procedures were similarly repeated by using urine of a pregnant woman instead of the standard sample solution. The results similar to those obtained in Example 3 were observed.

EXAMPLE 9

(a) *Serratia marcescens* was suspended at a concentration of 10% by weight in a phosphate acid-buffered saline solution (pH 7.2, PBS), and an equal amount of a 3% solution of formalin in PBS was added to the suspension and the mixture was agitated at 37° C. for 4 hours. Cells were collected by centrifugation, washed sufficiently with distilled water and suspended in distilled water at a concentration of 5% by weight. The suspension was heated at 120° C. for 20 minutes, and the cells were collected by centrifugation.

(b) The concentration of AFP in serum of a patient was determined in the same manner as described in Example 1 using the cells obtained in (a) above as the carrier. The results were similar to those obtained in Example 1.

EXAMPLE 10

This example illustrates a measurement reagent kit or pack for the measurement based on the agglutination reaction.

An HCG-measuring reagent kit comprising reagents described below was prepared.

(a) Five ampoules containing a lyophilized standard sample of HCG in an amount of 4 iu/ampoule.

(b) One bottle containing 1.5 ml of an anti-HCG antibody-sensitized latex agent.

(c) One bottle containing 3 ml of a glycine-buffered saline solution (pH 8.2).

(d) Five ampoules, each containing a lyophilized produce formed by freeze-drying 0.5 ml of 24% carbodiimide solution.

The measurement using this reagent kit was carried out, for example, according to the following procedures.

One ampoule of the standard sample of HCG was dissolved in a physiological saline solution to plot standard sample solutions at concentrations of 4, 2, 1, 0.5, and 0 iu/ml, respectively. 25 μl of the standard sample solution, 50 μl of the glycine-buffered saline solution, and 25 μl of the anti-HCG antibody-sensitized latex were put in a test tube and the reaction was carried out at room temperature under mild shaking for 40 minutes. 1.2 ml of a physiological saline solution were added to one ampoule of propyl carbodiimide as a solution of the fixing compound prior to completion of the above reaction. After the reaction, 0.1 ml of the fixing compound solution was added to the reaction mixture and the fixing reaction was carried out at room temperature for 20 minutes. After the fixing reaction, 4 ml of a physiological saline solution was added to the reaction mixture and the absorbancy at 500 nm was measured to plot a standard curve. The above procedures were repeated by using serum or urine of a patient instead of the standard sample solution, and the concentration of HCG in the serum or urine was determined.

EXAMPLE 11

This example illustrates a measurement reagent kit or pack for the measurement based on the agglutination-inhibition reaction.

An estriol-measuring reagent kit comprising the following reagents was prepared.

(a) Four bottles containing 1 ml each of standard sample solutions containing $E_3$ at concentrations of 200, 100, 50, and 25 ng/ml, respectively, in a physiological saline solution.

(b) One bottle containing 1.7 ml of an anti-estriol antibody-sensitized latex reagent.

(c) Six ampoules, each containing a lyophilized produce formed by freeze-drying 0.5 ml of 24% solution of propyl carbodiimide.

(d) One bottle containing 3.2 ml of a solution of $E_1$—BSA (5 μg/ml) as the agglutinating agent in a buffer solution.

(e) One graduation pipette (1.2 ml).

(f) Thirty dropping pipettes (25 μl/drop).

The measurement using this reagent kit was carried out, for example, according to the following procedures.

25 μl of the anti-estriol antibody-sensitized latex reagent and 50 μl of the solution of $E_1$—BSA (agglutinating agent) were put in a test tube, and 25 μl of the standard sample solution was added and reaction was carried out at room temperature under mild shaking for 40 minutes. Operations such as addition of the solution of the fixing compound were made according to the same procedures as described in Example 10, and the estriol concentration in serum or urine was determined. Since the graduated pipette and dropping pipettes were attached to the reagent kit, when this measurement kit was used, the measurement could easily be conducted even in a place where experiment tools or equipment were not furnished.

What is claimed is:

1. In a measuring method for determining an antigen, antibody, or antigen-antibody complex or conjugate comprising the steps of (1) causing an antigen-antibody reaction between (a) a sensitized carrier particle which is formed by binding (I) at least one substance selected from the group consisting of an antigen, antibody, and antigen-antibody complex and conjugate to (II) a carrier composed of an insoluble finely divided particle so that at least two units of said substance are bound to the particulate carrier and (b) at least one substance selected from the group consisting of an antigen, antibody, and antigen-antibody complex and conjugate to be determined and capable of causing an immunological reaction with said substance (I) bound to said sensitized carrier particle; and (2) measuring the absorbancy or turbidity of the reaction mixture formed in step (1) by irradiating said reaction mixture with a ray having a wavelength of from about 320 to about 2400 nm, wherein the measuring method is to determine the quantity or concentration of aggregate formed by said antigen-antibody reaction, the improvement which comprises fixing the aggregate formed by said antigen-antibody reaction by adding a fixing compound to the reaction mixture formed in the reaction system of step (1).

2. In a measuring method for determining an antigen, antibody, or antigen-antibody complex or conjugate comprising the steps of (1) causing an antigen-antibody reaction among (a) a sensitized carrier particle which is formed by binding (I) at least one substance selected from the group consisting of an antigen, antibody, and antigen-antibody complex and conjugate to (II) a carrier composed of an insoluble finely divided particle so that at least two units of said substance are bound to the particulate carrier, (b) at least one substance selected from the group consisting of an antigen, antibody, and antigen-antibody complex and conjugate to be determined and capable of causing the antigen-antibody reaction with said substance (I) bound to said sensitized carrier particle, and (c) an agglutinating agent which is at least one substance selected from the group consisting of an antigen, antibody, and antigen-antibody complex and conjugate and capable of causing an immunochemical reaction with said sensitized carrier particle (a); and (2) measuring the absorbancy or turbidity of the reaction mixture formed in step (1) by irradiating said reaction mixture with a ray having a wavelength of from about 320 to about 2400 nm, wherein the measuring method is to determine the quantity or concentration of aggregate formed by said antigen-antibody reaction, the improvement which comprises fixing the aggregate formed by said antigen-antibody reaction by adding a fixing compound to the reaction mixture formed in the reaction system of step (1).

3. The measuring method of claim 1 wherein said fixing compound is added to the reaction mixture after an antigen-antibody reaction has been caused in step (1).

4. The measuring method of claim 1 wherein said fixing compound is added simultaneously with the initiation of the antigen-antibody reaction in step (1) whereby formation of aggregates by said reaction and fixation of said aggregates are accomplished simultaneously.

5. The measuring method of claim 1 wherein said fixing compound is at least one member selected from the group consisting of polyfunctional compounds and protein denaturing agents.

6. The measuring method of claim 5 wherein said polyfunctional compound is selected from the group consisting of a carbodiimide, a dialdehyde, an imide ester, and an acylating agent.

7. The measuring method of claim 6 wherein said polyfunctional compound is selected from the group consisting of 1-ethyl-3-(3-dimethyl-aminopropyl)carbodiimide, 1-cyclohexyl-3-(2-morpholinoethyl)carbodiimide, glutaraldehyde, succinaldehyde, N-ethyl-5-phenylisoxazonium-3-sulfonate, and succinyl chloride.

8. The measuring method of claim 5 wherein said protein denaturing agent is selected from the group consisting of tannic acid, formalin, perchloric acid, trichloroacetic acid, thiocyanic acid, and thioglycolic acid.

9. The measuring method of claim 1 wherein said substance (b) is bound to a carrier composed of finely divided particles.

10. The measuring method of claim 2 wherein said fixing compound is added to the reaction mixture after an antigen-antibody reaction has been caused in step (1).

11. The measuring method of claim 2 wherein said fixing compound is added simultaneously with the initiation of the antigen-antibody reaction in step (1) whereby formation of aggregates by said reaction and fixation of said aggregates are accomplished simultaneously.

12. The measuring method of claim 2 wherein said fixing compound is at least one member selected from the group consisting of polyfunctional compounds and protein denaturing agents.

13. The measuring method of claim 12 wherein said polyfunctional compound is selected from the group consisting of a carbodiimide, a dialdehyde, an imide ester, and an acylating agent.

14. The measuring method of claim 13 wherein said polyfunctional compound is selected from the group consisting of 1-ethyl-3-(3-dimethyl-aminopropyl)carbodiimide, 1-cyclohexyl-3-(2-morpholinoethyl)carbodiimide, glutaraldehyde, succinaldehyde, N-ethyl-5-phenylisoxazonium-3sulfonate, and succinyl chloride.

15. The measuring method of claim 12 wherein said protein denaturing agent is selected from the group consisting of tannic acid, formalin, perchloric acid, trichloroacetic acid, thiocyanic acid, and thioglycolic acid.

16. The measuring method according to claim 2 wherein said substance (b) is bound to a carried composed of finely divided particles.

* * * * *

UNITED STATES PATENT AND TRADEMARK OFFICE
CERTIFICATE OF CORRECTION

PATENT NO. : 4,332,788
DATED : June 1, 1982
INVENTOR(S) : MOCHIDA, et al.

It is certified that error appears in the above—identified patent and that said Letters Patent is hereby corrected as shown below:

Column 10, line 56: Change "AFT" to -- AFP --;

Column 12, Table 2 (foot note): Change "lul" to -- liu --;

Column 17, Claim 9, line 2: Change "substance (b)" to -- substance (c) --;

Column 18, Claim 16, line 2: Change "substance (b)" to -- substance (c) --.

Signed and Sealed this

Fifteenth Day of March 1983

[SEAL]

Attest:

GERALD J. MOSSINGHOFF

Attesting Officer    Commissioner of Patents and Trademarks